United States Patent

De Boer et al.

[11] Patent Number: 5,821,310
[45] Date of Patent: Oct. 13, 1998

[54] ORGANOMETALLIC COMPOUNDS AND CATALYST COMPOSITIONS

[75] Inventors: Eric Johannes Maria De Boer; Bart Johan Ruisch; Lodewijk Schoon, all of Amsterdam, Netherlands

[73] Assignee: Shell Oil Company, Houston, Tex.

[21] Appl. No.: 671,911

[22] Filed: Jun. 28, 1996

[30] Foreign Application Priority Data

Jun. 28, 1995 [EP] European Pat. Off. ............. 95201766

[51] Int. Cl.$^6$ ........................... C08F 10/00; C08F 4/643; C07F 17/00
[52] U.S. Cl. ................. 526/127; 526/126; 526/134; 526/160; 526/170; 526/172; 526/348.2; 526/351; 526/943; 502/103; 502/117; 502/152; 502/153; 502/155; 556/7; 556/11; 556/12; 556/14; 556/20; 556/43; 556/52; 556/53; 556/58
[58] Field of Search ................................. 556/7, 12, 14, 556/20, 22, 23, 28, 43, 52, 58, 11, 53; 526/127, 133, 160, 170, 134, 172, 943; 585/520, 525, 526, 527

[56] References Cited

U.S. PATENT DOCUMENTS

| | | | |
|---|---|---|---|
| 3,663,635 | 5/1972 | Lassau et al. | 260/666 P |
| 5,434,116 | 7/1995 | Sone et al. | 526/133 X |
| 5,489,659 | 2/1996 | Sugano et al. | 526/127 |
| 5,554,775 | 9/1996 | Krishnamurti et al. | 556/7 |

FOREIGN PATENT DOCUMENTS

| | | |
|---|---|---|
| 0069951 | 7/1982 | European Pat. Off. . |
| 0129368 | 6/1984 | European Pat. Off. . |
| 0277003 | 1/1988 | European Pat. Off. . |
| 0277004 | 1/1988 | European Pat. Off. . |
| 0426637 | 10/1990 | European Pat. Off. . |
| 0540108 | 10/1992 | European Pat. Off. . |
| 0596553 | 10/1993 | European Pat. Off. . |
| WO 95/04087 | 7/1994 | WIPO . |

*Primary Examiner*—Fred Teskin

[57] ABSTRACT

There is provided an organometallic compound comprising a metal M of Group 3 to 6 of the Periodic Table or the Lanthanide series and at least one (hetero)cyclohexadienyl ligand of the general formula (I)

$$C_5AR_n$$

wherein A is an element chosen from Group 13 to 16 of the Periodic Table, R which can be connected to C or to A and which may form a bridge is independently hydrogen or an organic substituent which may contain one or more hetero-atoms and n is 3 plus the number of valencies of A. There is further provided the use of this compound as a catalyst, with a co-catalyst, in a process for the (co)oligomerisation or (co)polymerisation of olefinically unsaturated hydrocarbons.

27 Claims, No Drawings

ORGANOMETALLIC COMPOUNDS AND CATALYST COMPOSITIONS

FIELD OF THE INVENTION

This invention relates to new organometallic compounds and to catalyst compositions comprising these organometallic compounds, which compositions are useful for the (co) oligomerisation and (co)polymerization of olefinically unsaturated hydrocarbons (Ziegler-Natta type catalysis). The invention further relates to catalyst compositions comprising these new organometallic compounds and known co-catalysts.

BACKGROUND OF THE INVENTION

Ziegler-Natta catalysts have a long history. The first reports on homogeneous olefin polymerization catalysts composed of a Group 4 metal complex and an alkylaluminium compound as cocatalyst were published by Breslow and Newburg (J. Am. Chem. Soc. 79 1957 5072 and 81 1959 81). Subsequently, it was reported that the addition of small amounts of water to the above compositions increased the rate of polymerization (W.P. Long, J. Am. Chem. Soc. 81 1959 5312; Long and Breslow, J. Am. Chem. Soc. 82 1960 1953). Later, Sinn and Kaminsky (e.g. in W. Kaminsky, Adv. Organmetal Chemistry 18 1980 99) reacted the alkylaluminium with equimolar amounts of water to produce aluminoxane, which proved to be a much more effective cocatalyst. Currently, the best known aluminoxane cocatalyst is methyl aluminoxane (MAO). Still later, R.F. Jordan et al. (J. Am. Chem. Soc. 108 1986 1718 and 7410) replaced the cocatalyst by reacting the group 4 metal complex with a compound, the anion of which is substantially non-coordinating. K. Shelly and C.A. Reed (J. Am. Chem. Soc. 108 1986 3117) showed that the bulky carborate $B_{11}CH_{12}$ is "the least coordinating anion" and Turner (in EP-A 277003 and EP-A 277004) defined groups of bulky, substantially non-coordinating anions as cocatalysts with Group 4 metallocene catalysts.

The Group 4 metal compounds generally are metallocenes, containing in relation to the four valencies of the metal 1–4, in particular two, cyclopentadienyl ($C_5H_5$) rings, and 0–3, in particular also two, alkyl or halogen radicals. Several patent publications also claim similar Group 5 and 6 metallocenes, in addition to the still preferred Group 4 metallocenes.

Illustrative examples of patent publications relating to the more modern Ziegler-Natta catalysts and disclosing their use in the polymerization of olefins, in particular the production of solid, high-molecular polymers and copolymers of ethene, are:

EP-B 69951 to HOECHST, disclosing catalyst compositions of bis(cyclopentadienyl)zirconium- dichloride or -methylchloride with methyl aluminoxane;

EP-B 129368 to EXXON, disclosing catalyst compositions of substituted mono-, bis- and tri(cyclopentadienyl)-Group 4 metal halogenide or -hydrocarbide and an aluminoxane;

EP-A 277003 of EXXON, disclosing catalyst compositions of substituted or unsubstituted bis(cyclopentadienyl) Group 4 metal hydrocarbide with an anion containing a plurality of boron atoms which is bulky, labile and capable of stabilizing the metal cation;

EP-A 277004 of EXXON, disclosing catalyst compositions of substituted or unsubstituted bis(cyclopentadienyl) Group 4 metal hydrocarbide with an anion having a plurality of lipophilic radicals around a metal or metalloid ion, which anion is bulky, labile and capable of stabilizing the metal cation; and EP-B 426637 to FINA, disclosing a process for making catalyst compositions of substituted or unsubstituted bis (cyclopentadienyl) Group 4–6 metal halogenide, hydrocarbide, amide or hydride with an anion which is non-coordinated or only loosely coordinated to the metallocene cation - by reacting the metallocene with a compound of said anion and carbonium, oxonium or sulfonium cation.

Illustrative examples of recent patent applications which are directed to similar catalyst compositions and which disclose in particular their use for the preparation of lower-molecular, liquid (co)oligomers of ethene and (co)polymers of propene respectively are:

EP-A 596553 of SHELL, disclosing catalyst compositions of substituted bis(cyclopentadienyl) Group 4 metal halogenide or hydrocarbide with a bulky, labile and substantially non-coordinating anion wherein the substitution of each of the two cyclopentadienyl radicals is different; and EP-A 540108 of SHELL, disclosing a catalyst composition of substituted bis(cyclopentadienyl) Group 4 metal halogenide, hydrocarbyl, hydrocarbamide or hydride with aluminoxane wherein at least one cyclopentadienyl radical is substituted with a single optionally substituted aryl group.

All of the above work used the cyclopentadienyl metal complexes, known under the general name of metallocenes. While most of the above identified publications, as well as further similar ones, contain in their scope substituents on the cyclopentadienyl ring, and while these substitutions in some cases may include one or more hetero-atoms, the five-ring itself remained unmodified.

By contrast to the foregoing, WO 95/04087 of SHELL discloses a catalyst composition of a Group 4 or 5 metal complexed with substituted or unsubstituted heterocyclopentadienyl, the heteroatom in the five-ring being a Group 15 element, and a co-catalyst which may be of the non-ionic (such as aluminoxane) and/or of the bulky anion type.

The sheer abundance of similar disclosures in the same field is evidence to the fact that the ideal Ziegler-Natta type catalyst has not been found yet. There still exists a need for active, selective, versatile and stabile olefin polymerization catalysts.

SUMMARY OF THE INVENTION

It has now been found that by replacing at least one five-membered (hetero)cyclopentadienyl ring of the known catalyst compositions as broadly described above with a six-membered (hetero)cyclohexadienyl ring, the (hetero) atom being chosen from Group 13 to 16, a new and exceedingly versatile group of Ziegler-Natta type catalysts can be made. The introduction of an additional atom inside the ring offers more flexibility in tuning the properties of the catalysts.

Organometal compounds comprising at least one such (hetero)cyclopentadienyl ring in complex with a metal chosen from Groups 3 to 6 of the Periodic Table and the Lantanide series are believed to be novel.

DETAILED DESCRIPTION OF THE INVENTION

The present invention in its broadest definition therefore relates to an organometallic compound comprising a metal M of Group 3 to 6 of the Periodic Table or the Lanthanide series and at least one (hetero)cyclohexadienyl ligand of the general formula (I)

$$C_5AR_n$$

wherein A is an element chosen from Group 13 to 16 of the Periodic Table, R which can be connected to C or to A and which may form a bridge is independently hydrogen or an organic substituent which may contain one or more hetero-atoms and n is 3 plus the number of valencies of A, and a second component which acts as a co-catalyst. When R forms a bridge, it preferably connects the (hetero)cyclopentadienyl ring to a ligand which in turn is connected to the metal M via at least one carbon atom.

The Periodic Table referred to is the Periodic Table of Elements according to the IUPAC 1988 notation (IUPAC Nomenclature of Inorganic Chemistry 1990, Blackwell Publ., London).

Preferably, the metal M is chosen from the group of titanium, zirconium and hafnium and A is chosen from the group of boron, quaternary carbon, silicon, germanium, nitrogen, phosphorus, arsenic, oxygen and sulphur. More preferably, the metal M is titanium or zirconium and A is boron, quaternary carbon or silicon.

More in particular, the novel organometallic compounds according to the present invention have the general formula (II) or (III)

$$(C_5AR'_{n-p})_m R''_p (C_5AR'_{n-p}) MQ_q \qquad (II)$$

$$(C_4AR'_{n-p})_m R''_p (C_5AR'_{n-p}) MQ_q \qquad (III)$$

wherein A, M and n are as defined above, each R', which can be the same or different, is chosen from hydrogen or an organic substituent (optionally containing one or more hetero-atoms) having from 1 to 20 carbon atoms or two substituents together forming a fused $C_4$–$C_6$ ring, R" is a molecular fragment bridging two dienyl rings, each Q, which can be the same or different, which can be connected to a (hetero)cyclohexadienyl ring and two of which can be interconnected to form a ring, is chosen from the group of hydrogen, aryl, alkyl, alkenyl, alkylaryl, arylalkyl, alkyloxyl, aryloxyl, alkylazanyl, arylazanyl, alkylthiolyl, arylthiolyl, alkylphosphalyl, arylphosphalyl, alkylazanediyl, arylazanediyl, alkylphosphanediyl, arylphosphanediyl, (hetero)cyclodienyl, indenyl or fluorenyl, any of which having from 1 to 20 carbon atoms and optionally being further substituted, or halogen, oxygen or sulphur, p is 0 or 1, m is 1, 2, 3 or 4, q is 1, 2, 3 or 4, and m+1 plus the sum of the valencies of the Q groups equals the valency of the metal.

The bridging molecular fragment R", when present, may be positioned between two carbon atoms of heterocyclohexadienyl rings, between a carbon and a hetero-atom A, or between two hetero-atoms A.

When R' is positioned between two carbon atoms it can be chosen from the wide range known for bridging two cyclopentadienyl, indenyl or fluorenyl rings, such as those disclosed in EP-B 129368, EP-A 336127 and EP-A 528287. Well-known examples thereof are the groups of $C_1$–$C_4$ radicals chosen from alkylene, dialkyl germanium or silicone, alkyl phosphine or amine and in particular 1,2-$C_2H_4$, 1,3-[$(CH_2)_3$], $(CH_3)_2Si$, $(CH_3)_2Si(O)_2$, 1,2-[$(CH_3)_2Si]_2$, 1,2-$(CH_2)_2C_6H_4$, $(CH_3)_2C$, 1,3-[{$(CH_3)_2Si$}$_2O$], 1,2-{$(CH_3)_2SiO$} and 1,3-[$(CH_3)_2Si(CH_2)_2$].

The preferred metals M in the present invention are titanium, zirconium and hafnium.

The preferred Q radicals are hydrogen, methyl, ethyl, neopentyl, phenyl, benzyl and chloride.

The organometal complex according to the invention may contain from 1 to 5 of the above (hetero)cyclohexadienyl rings, with from zero to four (hetero)cyclopentadienyl rings and a number balancing the valency of the metal M of the reactive groups Q which may react with a cation. Therefore, organometal complexes containing only one (hetero) cyclohexadienyl ring are expressly within the scope of the invention. However, organometal complexes containing two (hetero)cyclohexadienyl rings, and those containing one such ring and one (hetero)cyclopentadienyl ring, are preferred.

The processing of the heterocyclohexadienyls to organometallic complexes can be done along traditional synthesis routes. For example, the (hetero)cylohexadienyl anions can be prepared and reacted with zirconium tetrachloride to afford the bis-(hetero)cyclohexadienyl zirconium dichlorides.

Preferably in formula (II) or (III), M is chosen from the group of titanium, zirconium and hafnium, x is 1 or 2 and each Q which can be the same or different and two of which can be interconnected to form a ring, is chosen from the group of hydrogen, aryl, alkyl, alkenyl, alkylaryl, arylalkyl, alkyloxyl, aryloxyl, alkylazanyl, arylazanyl, alkylthiolyl, arylthiolyl, alkylphosphalyl, arylphosphalyl, alkylazanediyl, arylazanediyl, alkylphosphanediyl, arylphosphanediyl, or cyclodienyl, any of which having from 1 to 20 carbon atoms and optionally being further substituted, or halogen, oxygen or sulphur, preferably from the group of hydrogen, halogen, R', $NR'_2$, $PR'_2$, OR' or SR', wherein R' is a hydrocarbyl or a cycloalkyl, optionally containing a heteroatom.

The novel compounds according to the invention are useful in catalyst compositions for the (co)oligomerisation or (co)polymerization of olefinically unsaturated hydrocarbons. In these catalyst compositions, co-catalysts are required.

The present invention therefore further concerns a catalyst composition for the (co)oligomerisation or (co)polymerization of olefinically unsaturated hydrocarbons, comprising a first component which is an organometallic compound as defined above and a second component which acts as a co-catalyst.

The co-catalyst can be a hydrocarbyl aluminum compound, in particular an aluminoxane.

Aluminoxanes are well known polymeric aluminum compounds, which can be represented by the general formulae (R—Al—O)$_n$ which represents a cyclic compound, and R(R—Al—O)$_n$—AlR$_2$, which represents a linear compound. In these general formulae R is an alkyl, preferably of 1–5 carbon atoms and n is 1–100, especially 5–20. The aluminoxanes are suitably prepared by reacting water with trialkylaluminium compounds, whereby usually a mixture of the linear and cyclic polymer is obtained.

The best known aluminoxane is methyl aluminoxane (MAO). Also effective is a mixture of methyl aluminoxane and isobutyl aluminoxane (IBAO).

Preferred organometallic complexes according to the invention (formula II) for combination with aluminoxanes contain at least two groups Q, being the same or different and chosen from hydrogen, alkyl, aryl, alkenyl, alkylaryl, arylalkyl or cyclopentadienyl, any of which having from 1 to 20 carbon atoms and optionally being further substituted, or halide.

The molar ratio of the aluminoxane to the organometallic complex according to the invention may vary between wide ranges. Suitably the molar ratio is within the range of from 2 to 10000, preferably from 50 to 2000, calculated as gram atoms of aluminum per gram atom of metal M.

The catalyst composition of the organometal complex of the present invention with the aluminoxane may be prepared prior to the contacting with the olefinically unsaturated compounds to be polymerized, or it may be prepared in situ i.e. in the presence of the feed. It is preferred to prepare this catalyst composition by mixing together the two components in solution in a solvent such as toluene to form a liquid catalyst system.

Alternatively, the co-catalyst is a compound capable of providing a bulky and substantially non-coordinating anion [An−], which co-catalyst reacts with the organometallic compound (first component) according to the invention to form an ionic compound of the general formula (IV) or (V)

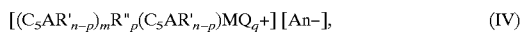

$$[(C_5AR'_{n-p})_mR''_p(C_5AR'_{n-p})MQ_q+] [An-], \qquad (IV)$$

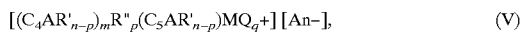

$$[(C_4AR'_{n-p})_mR''_p(C_5AR'_{n-p})MQ_q+] [An-], \qquad (V)$$

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal −1.

It will be appreciated that the ionic catalytic compound of formula (IV) or (V) can be produced in different ways.

One way to produce the ionic catalytic compound is by reacting an organometallic complex according to the invention with a compound of a bulky and substantially non-coordinating anion. The cation associated with the bulky anion should be capable of abstracting an anion from the organometal complex to form a (hetero)cyclohexadienyl ionic compound, rendering itself neutral. An illustrative example for such reactions is:

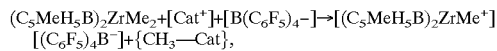

$$(C_5MeH_5B)_2ZrMe_2+[Cat^+]+[B(C_6F_5)_4-]\rightarrow [(C_5MeH_5B)_2ZrMe^+]\ [(C_6F_5)_4B^-]+\{CH_3-Cat\},$$

whereby, when the cation [Cat+] is for example [PhNH(CH$_3$)$_2$+], {CH$_3$—Cat} will become CH$_4$+PhN(CH$_3$)$_2$, and when the cation is [Ph$_3$C$^+$] {CH$_3$—Cat} will become Ph$_3$C—CH$_3$.

Preferably, the bulky and substantially non-coordinating anion is a carborane anion, suitably a carborane anion of the formula [B$_{11}$CH$_{12}$—]. Such carboranes are known and can be prepared by methods such as that of K. Shelly et al (J. Am. Chem. Soc. 107 1985 5955. other bulky boron containing anions are of the general formula [BR$_4$—], wherein R is C$_6$H$_5$, C$_6$F$_5$, 3,5-(CF$_3$)$_2$C$_6$H$_3$ and 4-FC$_6$H$_4$, such as the tetra(perfluorophenyl)boron anion.

The cation is suitably a proton-donating cation, preferably a quaternary ammonium cation such as a trialkylammonium cation, for example tri-n-butylammonium cation. Alternatively, a cation may be used which is not proton-donating, such as a metal cation e.g. a silver ion, or a triphenylcarbonium ion.

The catalyst composition may be formed by mixing together the organometallic complex and the compound of the bulky and substantially non-coordinating anion, preferably in solution in a suitable non-polar solvent such as toluene, chlorobenzene, an alkane or an alkene, to form a liquid catalyst system. The two components are generally employed in substantially equimolar amounts, although the molar ratio of the first component to the second component may vary within the range of from 0.1 to 5.0. Such a quantity of the catalyst system is usually employed in the reaction mixture as to contain from 10$^{-1}$ to 10$^{-7}$ gram atoms, in particular from 10$^{-3}$ to 10$^{-5}$ gram atoms, of the metal per mole of olefinically unsaturated hydrocarbon to be reacted.

Another way to produce the ionic catalyst is by reacting a organometallic compound according to the invention with a neutral, strongly Lewis acidic compound which is capable of abstracting one of the radicals Q of the organometallic compound, thereby also contributing a bulky and substantially non-coordinating anion to the completed catalyst compound. An illustrative example of such a reaction, related to the procedure described by X. Yang et al., J. Am. Chem. Soc. 113 1991 3623, is:

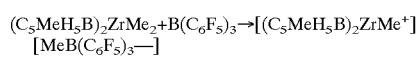

$$(C_5MeH_5B)_2ZrMe_2+B(C_6F_5)_3 \rightarrow [(C_5MeH_5B)_2ZrMe^+]\ [MeB(C_6F_5)_3-]$$

Although not required for catalytic activity, further components may be added to the catalytic composition according to the invention, for example in order to increase the solubility or the lifetime of the composition. For the ionic catalytic compositions, organoaluminium compounds in relatively small amounts are efficient solubilizing and scavenging agents. Examples of such organoaluminium compounds are trimethylaluminium, triethylaluminium, tri-isopropylaluminium, tri-isobutylaluminium, triphenylaluminium and diethylaluminium chloride.

The complete catalyst compositions according to the invention can be used in solution. Alternatively, the catalyst composition can be loaded on a solid carrier, in particular an inorganic oxide such as silica, alumina, silica/alumina, titania, zirconia, magnesia and the like, but resinous support materials such as polyolefins can also be used. Suitable supports are the materials, composed of aluminoxane and silica and marketed for example by WITCO GmbH, Bergkamen, Germany. Both neutral and ionic catalytic compositions as defined hereinbefore, containing the (hetero)cyclohexadienyl organometallic complexes according to the invention, can be combined with these materials to form solid catalytically active compositions.

A further aspect of the present invention is the process of (co)oligomerisation or (co)polymerization of one or more olefinically unsaturated hydrocarbon(s) in the presence of catalyst compositions as defined hereinbefore.

The (co)oligomerisation or (co)polymerization reaction according to the invention can be carried out in the liquid phase. When the catalyst compositions are loaded on an inert carrier the reaction is heterogeneous and can also be carried out in the gas phase. The reaction can be carried out in batch or continuous operation.

The oligomerisation or polymerization reaction is generally, although not necessarily, carried out in an inert liquid which is suitably also the solvent for the catalyst components. The reaction is suitably carried out at an elevated temperature, preferably in the range of from 20° to 175° C., more preferably at 50° to 150° C. The reaction is suitably carried out under conditions of moderately elevated pressure, preferably in the range of from 100 to 10000 kPa, more preferably from 500 to 6000 kPa. The optimum conditions of temperature and pressure used in a particular reaction system in order to maximize the yield of the desired oligomers or polymers can be readily established by those skilled in the art.

The starting reactants may be supplied to the reactor together with an inert diluent, such as nitrogen or helium when the reactant is gaseous, and a liquid solvent, e.g. the same solvent as that of the catalyst components, when the reactant is in the liquid form.

The reaction is preferably carried out in the absence of air or moisture.

Reaction times of from 1 minute to 5 hours have been found to be suitable, depending on the activity of the catalyst system and on the reaction conditions. When the reaction is homogeneous it can be terminated by adding to the reaction mixture a conventional catalyst deactivating agent (proton donor) such as water, methanol, or another alcohol. Alternatively, the reaction can simply be terminated by the introduction of air.

The products of the reaction are typically mixtures. They may be suitably recovered by separation techniques known in the art. If desired, unconverted starting material and products having a molecular weight outside the desired molecular weight may be recovered, processed if necessary and recycled to be used as starting material in a subsequent oligomerisation reaction.

The present invention has an outstanding versatility and the products may vary very widely in their molecular weight which may be from that of dimers of the starting olefins to polymers of over 1000000 daltons, and in their molecular composition. The properties of the products may be controlled by a proper choice of the catalyst composition, the starting material(s) and the reaction conditions. Also, when the presence of an unsaturated end group in the product is not a requirement, the molecular weight thereof can be controlled by adding hydrogen to the reaction mixture.

One example of a group of products are alkenes which are preferentially linear alpha alkenes having a chain length within the range of 5 to 24 carbon atoms, of which those having between 6 and 10 carbon atoms in the chain are currently particularly preferred. They are in great demand as intermediates for the preparation of detergents, lubricant additives and polyolefins.

Another example of a group of products are liquid atactic polymers, preferably having an olefinically unsaturated end group, more preferably a vinylidene end group, and a number average molecular weight of from 300 to 10000 daltons. Such liquid atactic vinylidene polymers, in particular those which are prepared from propylene, are useful as intermediates for the preparation of dispersants for lubricating oil compositions.

Yet another group of products are solid polymers.

The invention will be further illustrated by the following Examples.

EXAMPLE A

PREPARATION OF CATALYST PRECURSORS

A-1, Preparation of pentamethylcyclopentadienyl 1-methyl-1-boracyclohexadienyl zirconium dichloride, Cp*($C_5H_5BMe$)$ZrCl_2$.

Lithium 1-methyl-1-boracyclohexadienyl, Li[$C_5H_5BMe$] was prepared according to Herberich et al., *Organometallics* 1995, 14, 471–480. Li[$C_5H_5BMe$], 150 mg, was dissolved in diethylether, 20 ml, and to the solution pentamethylcyclopentadienyl zirconium trichloride, Cp*$ZrCl_3$, 500 mg, was added slowly. The reaction mixture was stirred for 24 hours and subsequently the volatiles removed under vacuum. The residue was dissolved in dichloromethane and the precipitate filtered off after centrifugation. The remaining solution was evaporated to dryness and the resulting solid material, A-1, isolated, 90 mg.

$^1$H-NMR ($CD_2Cl_2$, δ, ppm): 7.3–7.45(dd), 6.2(d), 6.07(t) (all resonances show additional small couplings), 2.0(s), 0.75(s). $^{11}$B-NMR ($CD_2Cl_2$, δ, ppm): 45.87.

A-2, Preparation of cyclopentadienyl 1-methyl-1-boracyclohexadienyl zirconium dichloride, Cp($C_5H_5BMe$)$ZrCl_2$.

Lithium 1-methyl-1-boracyclohexadienyl, Li[$C_5H_5BMe$] was prepared according to Herberich et al., *Organometallics* 1995, 14, 471–480. Li[$C_5H_5BMe$], 50 mg, was dissolved in diethylether and to the solution cyclopentadienyl zirconium trichloride, $CpZrCl_3$, 134 mg, was added slowly. The reaction mixture was stirred for 4 hours and subsequently the volatiles removed under vacuum. The residue was dissolved in dichloromethane/pentane mixture and the precipitate filtered off after centrifugation. The remaining solution was evaporated to dryness and the resulting solid material, A-2, isolated, 130 mg.

$^1$H-NMR ($CD_2CD_2$, δ, ppm): 7.78–7.74(dd), 6.76(m), 6.48(s), 6.22(d), 0.98(s)
$^{11}$B-NMR ($CD_2Cl_2$, δ, ppm): 45.52.

A-3, Preparation (in situ) of bis-(1-methyl-1-boracyclohexadienyl) zirconium dichloride, ($C_5H_5BMe$)$_2ZrCl_2$.

Lithium 1-methyl-1-boracyclohexadienyl, 10 mg, and zirconium tetrachloride, 11.9 mg, were reacted in $C_6D_6$, 2 ml. The reaction mixture was stirred for two hours during which time a fine precipitate and yellow solution formed. The reaction mixture was centrifuged, the solution decanted, and the solids washed with $C_6D_6$, 1 ml. The $C_6D_6$ solutions were combined and analyzed by NMR. The data are in agreement with the compound being A-3.

$^1$H-NMR ($C_6D_6$, δ, ppm): 7.20–7.08(m), 6.19–5.98(m), 0.98(s).
$^{11}$B-NMR ($C_6D_6$, δ, ppm): 45.08.

A-4, Preparation of pentamethylcyclopentadienyl 1-sila-1,1-dimethyl-2,3,4,5-tetraphenylcyclohexadienyl zirconium dichloride, Cp*(1-Si-1,1-$Me_2$-2,3,4,5-$Ph_4C_5$H)$ZrCl_2$.

1-Sila-1,1-dimethyl-2,3,4,5-tetraphenylcyclohexadienyl lithium was prepared by reaction of 1-sila-1,1-dimethyl-2,3,4,5-tetraphenylcyclohexadiene (prepared from 1,4-dilithio-1,2,3,4,-tetraphenylbutadienediyl and chloromethyldimethylchlorosilane, $Me_2Si(Cl)CH_2Cl$, see Nakadaira et al *J. Am. Chem. Soc.* 1974, 96, 5621–5622) with n-BuLi in THF at room temperature. Reaction of the silacyclohexadienyl anion, 0.15 g, with an equivalent amount of pentamethylcyclopentadienyl zirconium trichloride, Cp*$ZrCl_3$, in benzene, 30 ml, at room temperature. After stirring the reaction mixture for one hour the generated precipitate was removed by centrifugation and decanting the supernatant mother liquor. From this solution the volatiles were evaporated of and the remaining product was washed with hexane. The solid obtained after drying was isolated and characterized by NMR and identified as A-4.

$^1$H-NMR ($C_6D_6$, δ, ppm): 7.8–7.2(arom.), 6.83, 6.09, 2.75, 1.85, 0.49, 0.30.

A-5, Preparation of pentamethylcyclopentadienyl 1-sila-1,1-dimethyl-dibenzocyclohexadienyl zirconium dichloride, Cp*(1-Si-1,1-$Me_2C_{13}H_9$)$ZrCl_2$.

1-Sila-1,1-dimethyl-dibenzocyclohexadiene having the following structure was prepared by reaction of o,o'-dilithiobiphenyl with one equivalent of chloromethyldimethylchlorosilane, $Me_2Si(Cl)CH_2Cl$ in THF at −78° C. The reaction mixture was slowly warmed to room temperature and subsequently all volatiles were removed under vacuum.

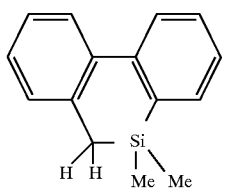

The obtained product was characterized by NMR which indicated that the product was almost pure silacyclohexadiene with structure shown in the Figure. The so obtained silacyclohexadiene was converted into the corresponding silacyclohexadienyl anion by reaction with one equivalent of n-BuLi in THF at room temperature. The anion was isolated and characterized by NMR. Reaction of the anion, 0.25 g, with one equivalent of pentamethylcyclopentadienyl zirconium trichloride, Cp*ZrCl$_3$, 0.2 g, in a similar procedure as described for A-4, afforded A-5 which was characterized by NMR.

$^1$H-NMR (C$_6$D$_6$, δ, ppm): 7.6–6.7(arom.), 3.79, 1.74, 0.63, 0.24.

EXAMPLE B

POLYMERIZATION EXPERIMENTS

B-1: Propene Polymerizations

Description of polymerization experiments.

A 1 liter autoclave containing 200 ml of toluene and 3.5 ml of a solution containing 10% MAO was charged with 600 kPa of propene at 45° C. The system was allowed to reach equilibrium while the pressure was kept at 600 kPa. Subsequently, catalyst precursor, 0.01 mMol dissolved in 10 ml of toluene were added to the autoclave by means of a catalyst injection system. After the reaction was stopped by release of excess propylene, the autoclave contents were treated with a small amount of water, filtrated to remove the solids, dried over MgSO$_4$, the volatiles removed under vacuum, and the products analyzed. Alternatively, in the case of low molecular weight products, the reaction contents after reaction were weighed and the yields were calculated by subtraction of the weight of the reaction components at the start of the reaction.

B-1-1: Catalyst precursor A-1, Cp*(C$_5$H$_5$BMe)ZrCl$_2$, 0.01 mMol

Reaction time was 60 minutes. The yield of product was 92 g. NMR analysis of the product was in agreement with an atactic product of molecular weight 250. (Turnover=200.000 Mol C$_3$=/Mol Zr.hr.)

B-1-2: Catalyst precursor A-2, Cp(C$_5$H$_5$BMe)ZrCl$_2$, 0.005 mMol

Reaction time was 60 minutes. The yield of product was 56 g. NMR analysis of the product was in agreement with an atactic product of molecular weight 143. (Turnover=268.000 Mol C$_3$=/Mol Zr.hr.)

B-1-3: Catalyst precursor A-3, (C$_5$H$_5$BMe)$_2$ZrCl$_2$, 1/3 of the product prepared in situ as described under A-3.

Reaction time was 60 minutes. Yield of product 2.1 g. NMR analysis of the product was in agreement with an atactic product of molecular weight 160. (Turnover=5.000 Mol C$_3$=/Mol Zr.hr.)

B-1-4: Catalyst precursor A-2, Cp(C$_5$H$_5$BMe)ZrCl$_2$, 0.005 mMol

Instead of cocatalyst MAO a cocatalyst was used which was a 1:1 mixture of MAO and hexameric isobutylalumoxane. The Zr:Al ratio was kept at 1:500.

Reaction time was 60 minutes. The yield of product was 43.6 g. NMR analysis of the product was in agreement with an atactic product of molecular weight 250. (Turnover= 194.000 Mol C$_3$=/Mol Zr.hr.)

B-1-5 (Comparative example) : Catalyst precursor Cp$_2$ZrCl$_2$, 0.005 mMol.

Reaction time was 60 minutes. Yield of product was 18 g. NMR analysis of the product was in agreement with an atactic product of molecular weight 910. (Turnover=85.000 Mol C$_3$=/Mol Zr.hr.)

B-2: Ethylene polymerizations

Performed in a procedure similar to propylene polymerizations except that ethylene at 300 kPa was used instead of propene, and the products were isolated by filtration of the reactor contents.

B-2-1: Catalyst precursor A-1, Cp*(C$_5$H$_5$BMe)ZrCl$_2$, 0.008 mMol

Reaction time was 7 minutes. The yield of product was 9.8 g. Melting point of polymer 114° C. (Turnover=385.000 Mol C$_2$=/Mol Zr.hr.)

B-2-2: Catalyst precursor A-4, Cp*(1-Si-1,1-Me$_2$-2,3,4,5-Ph$_4$C$_5$H)ZrCl$_2$, 0.006 mMol Reaction time was 30 minutes. The yield of product was 0.8 g, melting point 116.8° C. (Turnover=6.000 Mol C$_2$=/Mol Zr.hr.)

B-2-3: Catalyst precursor A-5, Cp*(1-Si-1,1-Me$_2$C$_{13}$H$_9$)ZrCl$_2$, 0.01 mMol Reaction time was 30 minutes. The yield of product was 9.9 g, melting point 123.9° C. (Turnover=71.000 Mol C$_2$=/Mol Zr.hr.)

B-3: Ethylene/1-octene copolymerization

Similar to ethylene polymerizations except that octene-1 was introduced in the reactor as part of the solvent. The total volume of solvent was kept constant.

B-3-1: Catalyst precursor A-1, Cp*(C$_5$H$_5$BMe)ZrCl$_2$, 0.01 mMol

Amount of 1-octene 20 ml, reaction time was 6.5 minutes. The yield of copolymer product was 29.4 g. Melting point 116° C. (Turnover=1.000.000 Mol C$_2$=/Mol Zr.hr assuming ethylene as the only monomer.)

B-3-2: Catalyst precursor A-2, Cp(C$_5$H$_5$BMe)ZrCl$_2$, 0.01 mMol

Amount of 1-octene 20 ml, reaction time was 6.5 minutes. The yield of copolymer product was 40 g. Melting point 114° C. (Turnover=1.330.000 Mol C$_2$=/Mol Zr.hr assuming ethylene as the only monomer.)

B-3-3 (Comparative example) : Catalyst precursor Cp$_2$ZrCl$_2$, 0.01 mMol.

Amount of 1-octene 20 ml, reaction time 6.5 minutes. The yield of copolymer product was 30 g. Melting point 116.5° C. (Turnover=1.020.000 Mol C$_2$=/Mol Zr.hr assuming ethylene as the only monomer.)

B-4: 1-Octene polymerization

B-4-1: Catalyst precursor A-2, Cp(C$_5$H$_5$BMe)ZrCl$_2$, 0.01 mMol.

1-Octene, 5 ml, were mixed with 5 mMol MAO in toluene, 11 ml. After 15 minutes stirring at room temperature, catalyst precursor A-2, 3.4 mg dissolved in 1.5 ml toluene, was added in one shot. The reaction mixture was stirred 2 hour and analyzed by GC and NMR. The analyses showed quantitative conversion of starting 1-octene and formation of an oligomeric product with average molecular weight of 250 and a 2,2-disubstituted olefinic end-group.

We claim:

1. A catalyst composition produced by combining a first component which is an organometallic compound of a metal M of Group 3 to 6 of the Periodic Table or the Lanthanide series and at least one (hetero)cyclohexadienyl ligand of the formula (I)

$$C_5AR_n \qquad (I)$$

wherein A is an element chosen from quaternary carbon and silicon, R which can be connected to C or to A and which may form a bridge is independently hydrogen or an organic substituent which may contain one or more hetero-atoms and n is 3 plus the number of valencies of A, and a second component which acts as a co-catalyst.

2. The catalyst composition according to claim 1, characterized in that the first component is of the formula (II)

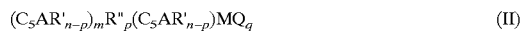

$$(C_5AR'_{n-p})_mR''_p(C_5AR'_{n-p})MQ_q \qquad (II)$$

wherein A, M and n are as defined above, each R', which can be the same or different, is chosen from hydrogen or an organic substituent, optionally containing one or more hetero-atoms, having from 1 to 20 carbon atoms or two substituents together forming a fused $C_4$–$C_6$ ring, R" is a molecular fragment bridging two dienyl rings, each Q, which can be the same or different, and two of which can be interconnected to form a ring, is chosen from the group of hydrogen, aryl, alkyl, alkenyl, alkylaryl, arylalkyl, alkyloxyl, aryloxyl, alkylazanyl, arylazanyl, alkylthiolyl, arylthiolyl, alkylphosphalyl, arylphosphalyl, alkylazanediyl, arylazanediyl, alkylphosphanediyl, arylphosphanediyl, (hetero)cyclodienyl, indenyl or fluorenyl any of which having from 1 to 20 carbon atoms and optionally being further substituted, or halogen, oxygen or sulphur, p is 0 or 1, m is 0, 1, 2, 3 or 4, q is 1, 2, 3 or 4, and m+1 plus the sum of the valencies of the Q groups equals the valency of the metal.

3. The catalyst composition according to claim 2, wherein m is 1 and p is 0.

4. The catalyst composition according to claim 2, wherein m is 0, p is 0 and one Q is (hetero)cyclopentadienyl.

5. A catalyst composition according to claim 1, characterized in that the co-catalyst is a hydrocarbyl aluminum compound.

6. The catalyst composition according to claim 1, characterized in that the co-catalyst is an aluminoxane.

7. The catalyst composition according to claim 1, characterized in that the co-catalyst is a compound capable of providing a bulky and substantially non-coordinating anion [An⁻], which co-catalyst reacts with the organonometallic compound to form an ionic compound of the formula (IV)

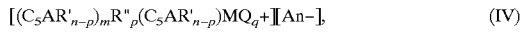   (IV)

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal –1.

8. The catalyst composition according to claim 7, characterized in that the anion [An–] is of an organoboron compound.

9. The catalyst composition according to claim 1, characterized in that it is loaded on a solid, inert carrier material.

10. The catalyst composition according to claim 1, characterized in that R forms a bridge to a ligand which in turn is coordinated to a metal M via at least one carbon atom.

11. A process for the (co)oligomerisation or (co) polymerization of olefinically unsaturated hydrocarbons, characterized in that it is performed in the presence of a catalyst composition according to claim 1.

12. The catalyst composition of claim 1, characterized in that the metal M is chosen from the group of titanium, zirconium and hafnium.

13. The catalyst composition according to claim 12, characterized in that the co-catalyst is a compound capable of providing a bulky and substantially non-coordinating anion [An⁻], which co-catalyst reacts with the organonometallic compound to form an ionic compound of the formula (IV)

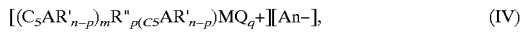   (IV)

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal –1.

14. The catalyst composition according to claim 13, characterized in that the anion [An–] is of an organoboron compound.

15. The catalyst composition according to claim 2, characterized in that the co-catalyst is a compound capable of providing a bulky and substantially non-coordinating anion [An⁻], which co-catalyst reacts with the organonometallic compound to form an ionic compound of the formula (IV)

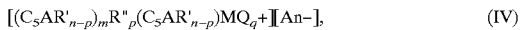   (IV)

wherein the components of the cation are as defined hereinbefore (formula II ) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal –1.

16. The catalyst composition according to claim 15, characterized in that the anion [An–] is of an organoboron compound.

17. The catalyst composition according to claim 3, characterized in that the co-catalyst is a compound capable of providing a bulky and substantially non-coordinating anion [An⁻], which co-catalyst reacts with the organonometallic compound to form an ionic compound of the formula (IV)

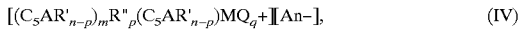   (IV)

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal –1.

18. The catalyst composition according to claim 13, characterized in that the anion [An–] is of an organoboron compound.

19. The catalyst composition according to claim 4, characterized in that the co-catalyst is a compound capable of providing a bulky and substantially non-coordinating anion [An⁻], which co-catalyst reacts with the organonometallic compound to form an ionic compound of the formula (IV)

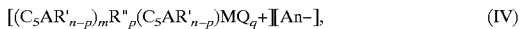   (IV)

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal –1.

20. The catalyst composition according to claim 17, characterized in that the anion [An–] is of an organoboron compound.

21. The catalyst composition according to claim 1, characterized in that the first component is of the formula (III)

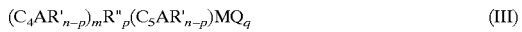   (III)

wherein A, M and n are as defined above, each R', which can be the same or different, is chosen from hydrogen or an organic substituent, optionally containing one or more heteroatoms, having from 1 to 20 carbon atoms or two substituents together forming a fused $C_4$–$C_6$ ring, R" is a molecular fragment bridging two dienyl rings, each Q, which can be the same or different, and two of which can be interconnected to form a ring, is chosen from the group of hydrogen, aryl, alkyl, alkenyl, alkylaryl, arylalkyl, alkyloxyl, aryloxyl, alkylazanyl, arylazanyl, alkylthiolyl, arylthiolyl, alkylphosphalyl, arylphosphalyl, alkylazanediyl, arylazanediyl, alkylphosphanediyl, arylphosphanediyl, or (hetero)cyclodienyl, indenyl or fluorenyl, any of which having from 1 to 20 carbon atoms and optionally being father substituted, or halogen, oxygen or sulphur, p is 0 or 1, m is 0, 1, 2, 3 or 4, q is 1, 2, 3 or 4, and m+1 plus the sum of the valencies of the Q groups equals the valency of the metal.

22. The catalyst composition according to claim 1, characterized in that the co-catalyst is a compound capable of providing a bulky and substantially non-coordinating anion [An⁻], which co-catalyst reacts with the organonometallic compound to form an ionic compound of the formula (V)

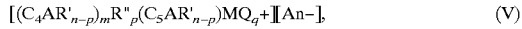

$$[(C_4AR'_{n-p})_m R''_p (C_5AR'_{n-p})MQ_q+][An-], \qquad (V)$$

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal −1.

23. The catalyst composition according to claim 22, characterized in that the anion [An−] is of an organoboron compound.

24. The catalyst composition according to claim 12, characterized in that the co-catalyst is a compound capable of providing a bulky and substantially non-coordinating anion [An⁻], which co-catalyst reacts with the organonometallic compound to form an ionic compound of the formula (V)

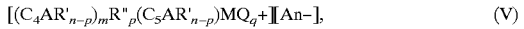

$$[(C_4AR'_{n-p})_m R''_p (C_5AR'_{n-p})MQ_q+][An-], \qquad (V)$$

wherein the components of the cation are as defined hereinbefore (formula II) with the proviso that at least one Q is chosen from the group of hydrogen, aryl, alkyl, alkenyl, alkylaryl, aryalkyl or cyclodienyl, any of which having from 1 to 20 carbon atoms and optionally being further substituted and m+1 plus the sum of the valencies of the Q groups equals the valency of the metal −1.

25. The catalyst composition according to claim 24, characterized in that the anion [An−] is of an organoboron compound.

26. The catalyst composition according to claim 21, characterized in that the co-catalyst is a compound capable of providing a bulky and substantially non-coordinating anion [An⁻], which co-catalyst reacts with the organonometallic compound to form an ionic compound of the formula (V)

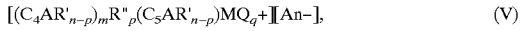

$$[(C_4AR'_{n-p})_m R''_p (C_5AR'_{n-p})MQ_q+][An-], \qquad (V)$$

wherein the components of the cation are as defined hereinbefore (formula II) with the proviso that at least one Q is chosen from the group of hydrogen, aryl, alkyl, alkenyl, alkylaryl, arylalkyl or cyclodienyl, any of which having from 1 to 20 carbon atoms and optionally being further substituted and m+1 plus the sum of the valencies of the Q groups equals the valency of the metal −1.

27. The catalyst composition according to claim 26, characterized in that the anion [An−] is of an organoboron compound.

* * * * *